(12) United States Patent
Faiyaziannasab

(10) Patent No.: US 9,180,320 B2
(45) Date of Patent: Nov. 10, 2015

(54) ALCOHOL-IN-OIL TYPE EMULSION COMPRISING A MULTIVALENT METAL SALT

(75) Inventor: Flora Faiyaziannasab, Copenhagen (DK)

(73) Assignee: RIEMANN TRADING APS, Hillerod (DK)

( * ) Notice: Subject to any disclaimer, the term of this patent is extended or adjusted under 35 U.S.C. 154(b) by 1849 days.

(21) Appl. No.: 12/158,254

(22) PCT Filed: Dec. 27, 2006

(86) PCT No.: PCT/DK2006/050085
§ 371 (c)(1),
(2), (4) Date: Sep. 19, 2008

(87) PCT Pub. No.: WO2007/073740
PCT Pub. Date: Jul. 5, 2007

(65) Prior Publication Data
US 2009/0010974 A1    Jan. 8, 2009

Related U.S. Application Data

(60) Provisional application No. 60/754,313, filed on Dec. 29, 2005.

(30) Foreign Application Priority Data

Dec. 29, 2005  (DK) ................................ 2005 01849

(51) Int. Cl.
| | | |
|---|---|---|
| *A61K 8/30* | (2006.01) | |
| *A61Q 5/12* | (2006.01) | |
| *A61K 9/00* | (2006.01) | |
| *A61Q 15/00* | (2006.01) | |
| *A61K 8/06* | (2006.01) | |
| *A61K 8/19* | (2006.01) | |
| *A61K 8/26* | (2006.01) | |
| *A61K 8/28* | (2006.01) | |
| *A61K 8/34* | (2006.01) | |

(52) U.S. Cl.
CPC . *A61Q 15/00* (2013.01); *A61K 8/06* (2013.01); *A61K 8/064* (2013.01); *A61K 8/19* (2013.01); *A61K 8/26* (2013.01); *A61K 8/28* (2013.01); *A61K 8/34* (2013.01); *A61K 8/342* (2013.01)

(58) Field of Classification Search
CPC ............ A61K 8/28; A61K 8/34; A61K 8/342
USPC .................................... 424/401, 70.22, 70.27
See application file for complete search history.

(56) References Cited

U.S. PATENT DOCUMENTS

| | | | | |
|---|---|---|---|---|
| 4,202,879 | A | * | 5/1980 | Shelton ............................ 424/66 |
| 4,435,382 | A | * | 3/1984 | Shin et al. ........................ 424/66 |
| 5,102,656 | A | | 4/1992 | Kasat |
| 5,143,718 | A | | 9/1992 | Bar-Shalom et al. |
| 5,194,249 | A | * | 3/1993 | Drucker et al. .................. 424/68 |
| 5,198,416 | A | | 3/1993 | Hale et al. |
| 5,665,368 | A | * | 9/1997 | Lentini et al. ................. 424/401 |
| 5,788,956 | A | | 8/1998 | De Lacharriere et al. |
| 6,271,295 | B1 | | 8/2001 | Powell et al. |
| 6,399,049 | B1 | * | 6/2002 | Swaile et al. .................... 424/65 |
| 6,613,312 | B2 | * | 9/2003 | Rizvi et al. ...................... 424/65 |
| 2002/0886039 | | * | 7/2002 | Lee et al. ....................... 424/401 |
| 2006/0140891 | A1 | * | 6/2006 | Nambu et al. .................... 424/65 |
| 2006/0182773 | A1 | * | 8/2006 | Bruning et al. ............... 424/401 |

FOREIGN PATENT DOCUMENTS

| | | |
|---|---|---|
| DE | 196 31 792 A1 | 8/1996 |
| DE | 196 43 063 A1 | 10/1996 |
| EP | 0 386 018 B1 | 3/1993 |
| EP | 0875235 B1 * 3/1998 | ............... A61K 7/06 |
| EP | 0 875 235 B1 | 12/2003 |
| JP | 2000-017174 | 1/2000 |

OTHER PUBLICATIONS

Patent Abstracts of Japan, vol. 2003, No. 12, Dec. 5, 2003 & JP 2005 013894 A, Jan. 20, 2005 *Abstract.
Cosmetics, Jan. 18, 2001, pp. 509-515.
Notice of Reasons for Rejection Japanese Patent Application No. 2008-547856 dated Aug. 9, 2011.

* cited by examiner

*Primary Examiner* — San-Ming Hui
(74) *Attorney, Agent, or Firm* — Foley & Lardner LLP

(57) ABSTRACT

The present invention relates to emulsion science, especially within the area of alcohol-in-oil type emulsion, where the level of ions comprised in the alcohol-in-oil type emulsion is relatively high. In particular, the invention relates to a stable alcohol-in-oil type emulsion comprising a multivalent metal salt that may act as an antiperspirant.

35 Claims, No Drawings

ALCOHOL-IN-OIL TYPE EMULSION COMPRISING A MULTIVALENT METAL SALT

FIELD OF INVENTION

The present invention relates to the field of emulsion type science, in particular with respect of providing stable alcohol-in-oil type emulsions comprising substances that provide a high level of electrolytes. Typically, the high level of electrolytes may be obtained by adding a multivalent metal salt to the alcohol-in-oil type emulsion.

BACKGROUND

Perspiration or sweat production is a completely natural physiological process made by the animal body and many people sweat more than they realise. It may come as a surprise to most people that the average person produces ½ to 1 liter sweat every day.

Human sweat itself is largely odorless. The principal cause of body odor are bacteria thriving in hot, humid environments such as the human underarm, which has a high density of sweat glands and is relatively occluded, which may be caused by an excessive production of sweat. The armpits are among the consistently warmest areas on the surface of the human body, and sweat glands provide moisture. Armpit hair adds to the odor because of the increased surface area.

The odor is seen as negative in most cultures, hence many people have a desire to eliminate or suppress it. One obvious way to reduce odor is to remove some, or all, of the underarm hair. Another way, or an additional way, to reduce the odor and the concentrated sweat production is to temporary plug the sweat duct causing the flow of sweat to the skin's surface to stop or to be reduced. This temporary plug may be provided by the use of an antiperspirant.

Antiperspirants are formulations having an aluminum-based compound as their main "active" ingredient, which can be any number of compounds within an established concentration and dosage form. The active ingredient gives antiperspirants their sweat-blocking ability by forming a temporary plug within the sweat duct that stops the flow of sweat to the skin's surface.

Thus, antiperspirant formulations may prevent odor and reduce sweat produced by the body.

EP 0 386 018 describes an efficient antiperspirant composition, wherein a metal salt is combined with a buffer salt suspended in alcohol. However, this composition has the drawback of developing sedimentation of the suspended particles during storage. This sedimentation causes an inhomogeneous dosing of the antiperspirant and leakage of the composition from the roller-ball of the device.

During production of products, it may be necessary to mix two or more types of liquid which as such are not mixable. To overcome this, liquids may be mixed in an emulsion where a temporary or permanent dispersion of an oil or another hydrophobic material in an aqueous solution, or vice versa, forming an oil-in-water emulsion or a water-in-oil emulsion. Generally, such oil-in-water or water-in-oil emulsions are capable of providing a stable solution.

Thus, it is suggested to provide a different system, such as an alcohol-in-oil type emulsion. This alcohol-in-oil type emulsion is not an emulsion as such because of the lack of water. However, it is a mixture of two types of liquid which as such are not mixable, namely a lower alcohol and an oil. However, it is established knowledge in the art that such kind of alcohol-in-oil type emulsions containing high levels of particles, e.g. multivalent metal ions, are considered as being unstable.

To improve the chemical stability of suspended particles that will release hydrochloric acid in presence of water, there is a need for a water-free composition, such as a alcohol-in-oil type emulsion. At the same time the water-free emulsion must be stable even in presence of a high level of electrolytes to provides a homogeneous distribution of the suspended particles.

SUMMARY OF INVENTION

With the aim of providing an improved emulsion type mixture that has improved stability during storage, avoiding precipitation and sedimentation of components and providing an homogenous composition, a first aspect of the present invention provides an alcohol-in-oil type emulsion comprising i) a multivalent metal salt, ii) a lower-alcohol phase, and iii) an oil phase.

In another aspect of the present invention a method for producing an alcohol-in-oil type emulsion is provided. The method comprises the steps of:
  (i) providing an oil phase,
  (ii) providing a suspension of a multivalent metal salt in an alcohol phase,
  (iii) mixing the oil phase provided in step (i) with the suspension provided in step (ii) to obtain a mixture,
  (iv) providing a further suspension of a multivalent metal salt in an alcohol phase,
  (v) mixing the mixture obtained in step (iii) with the further suspension of the multivalent metal salt in an alcohol phase provided in step iv) to obtain the alcohol-in-oil type emulsion.

In yet another aspect of the present invention an antiperspirant is provided. The antiperspirant comprises: (i) an aluminium salt, (ii) a lower alcohol phase, and (iii) an oil phase.

DETAILED DESCRIPTION OF THE INVENTION

The inventor of the present invention has found that an alcohol-in-oil type emulsion according to the present invention provide a stable homogenous emulsion type even when the emulsion type contains a high level of ions, such as a multivalent metal salt and where the precipitation and sedimentation of e.g. multivalent metal ions is limited or avoided.

In the present context the term "precipitation" relates to formation of particles in the mixture, such as in the alcohol-in-oil type emulsion. Precipitation can occur when an insoluble substance is formed in the solution due to a reaction or by agglomeration of suspended particles. In most situations, the solid forms ("falls") out of the solute phase or the suspension, and sinks to the bottom of the mixture or the alcohol-in-oil type emulsion.

In the present context the term "sedimentation" relates to the deposition of a particulate matter as a layer of solid particles on the bed or bottom of a body of a liquid, such as an alcohol-in-oil type emulsion. Sedimentation is the deposition by settling of a suspended material.

An Alcohol-in-Oil Emulsion

In a first aspect of the present invention an alcohol-in-oil type emulsion is provided. The emulsion type comprises a multivalent metal salt, a lower-alcohol phase, and an oil phase. In this aspect the alcohol-in-oil type emulsion has a viscosity sufficient to maintain the multivalent metal salt suspended homogeneously during storage. The alcohol-in-oil type emulsion has the clear advantage of being free or essentially free of water resulting in a good chemical stability of the suspended multivalent metal salt. It is to be understood that the alcohol-in-oil type emulsion of the present invention is stable despite the high ion level.

A Method of Preparing the Alcohol-in-Oil Emulsion

In another aspect of the present invention, a method is provided for producing an alcohol-in-oil type emulsion, wherein said method comprising the steps of:
  (i) providing an oil phase,
  (ii) providing a suspension of a multivalent metal salt in an alcohol phase,
  (iii) mixing the oil phase provided in step (i) with the suspension provided in step (ii) to obtain a mixture,
  (iv) providing a further suspension of a multivalent metal salt in an alcohol phase, and
  (v) mixing the mixture obtained in step (iii) with the further suspension of the multivalent metal salt in an alcohol phase provided in step iv) to obtain the alcohol-in-oil type emulsion.

Though an alcohol-in-oil type emulsion is known in the art, it is widely acknowledged that high level of ions is not compatible with a stable alcohol-in-oil type emulsion. To provide a stable emulsion according to the present invention, there are several actions that may be noticed. According to the invention in the first step i) an oil phase is provided. In the second step ii) a suspension of a multivalent metal salt in an alcohol phase is provided. To obtain a better and more homogenous distribution of the multivalent metal salt, it may be preferred that in the third step iii) where the oil phase is added to the suspension, the oil phase provided in step i) is added gently to the suspension of a multivalent metal salt provided in step ii) to obtain the alcohol-in-oil type emulsion.

In an embodiment of the present invention the metal compound comprised in the suspension of the multivalent metal salt provided in step ii) is typically an aluminium salt, such as a salt comprising an active antiperspirant salt. However, in other embodiments other metal salts providing a high ion level can be used if such a composition will benefit from being formulated as a stable alcohol-in-oil type emulsion. In such an embodiment, the mixture obtained in step iii) may be suitable for the given propose of the alcohol-in-oil type emulsion provided, such as being used as an antiperspirant. In such a case steps iv) and v) are optional steps and may be excluded from the method.

In yet an embodiment of the present invention it may be advantages to add the oil phase to the multivalent metal salt mixed with the alcohol phase by 2 or more sequences, such as in 3 or more sequences, e.g. in 4 or more sequences, such as in 5 or more sequences.

Step v) of the process, may be performed by adding the further suspension provided in step iv) to the mixture obtained in step iii) to obtain the alcohol-in-oil type emulsion. Again, to obtain a better and more homogenous distribution of the multivalent metal salt, the further suspension provided in step iv) may be added gently to the mixture obtained in step iii).

In a typical embodiment, the multivalent metal salt present in the suspension provided in step ii) and/or step iv) comprises a di- or tri- or tetra-valence metal-ion.

In one embodiment, the multivalent metal salt in step ii) may be a metal salt of an organic acid. Such a metal salt of an organic acid has the function of a buffer salt, which reacts with a strong acid, such as hydrochloric acid, that may be a reaction product of the active metal salt. By means of this buffer salt an adverse effect, such as skin irritation, due to e.g. free hydrochloric acid is limited or even avoided.

In one embodiment the multivalent metal salt provided in step ii) may be a metal salt of an organic acid, such as aluminium lactate or a hydrate thereof. In this embodiment, the metal salt of an organic acid functions as a buffer salt.

In one embodiment of the present invention the multivalent metal salt comprised in the further suspension in step iv) may be a metal salt of an inorganic acid. Typically, a multivalent metal salt of an inorganic acid has the function of an active multivalent metal salt. Such an active multivalent metal salt may in some embodiments be a multivalent metal salt providing an antiperspirant effect. Contacted by water, such a multivalent metal salt typically reacts with the water or moisture giving a strong acid, such as hydrochloric acid, as a reaction product.

In one embodiment the multivalent metal salt in step ii) may be a multivalent metal salt of an inorganic acid. Such a multivalent metal salt of an inorganic acid has the function of being an active multivalent metal salt. Such an active multivalent metal salt is in some embodiments a multivalent metal salt providing an antiperspirant effect. Contacted by water such a multivalent metal salt typically reacts with the water or moisture giving a strong acid, such as hydrochloric acid, as a reaction product.

In one embodiment, the multivalent metal salt is an aluminium chloride.

In one embodiment of the present invention, the multivalent metal salt comprised in the further suspension in step iv) is a multivalent metal salt of an organic acid, which reacts with a strong acid, such as hydrochloric acid, that may be a reaction product of the active metal salt and e.g. water. By means of this buffer salt an adverse effect, such as skin irritation, due to e.g. free hydrochloric acid is limited or even avoided.

In one embodiment the multivalent metal salt provided in step ii) may be aluminium lactate or a hydrate thereof. In this embodiment, the multivalent metal salt of an organic acid functions as a buffer salt.

In the embodiments where an acid, such as hydrochloric acid, is liberated resulting from the multivalent metal salt when contacted with water, the product according to the invention will have a characteristically low pH value when measuring the pH. When measuring the pH on a mixture of 50(w/w) % of the alcohol-in-oil type emulsion, such as is obtained in step v) mixed with 50(w/w) % water, the pH is in the range of 0-5, such as in the range of 0-4, such as in the range of 0-3, such as in the range of 1-5, such as in the range of 2-3. When measuring the pH on a mixture of 50% (w/w) alcohol-in-oil type emulsion and 50% (w/w) water, the temperature of the mixture must be 20° C.

In the embodiments where an acid, such as hydrochloric acid is liberated by contact with water, it is characteristic for the product that the conductivity will be high due to the high level of ions. When measuring the conductivity on a mixture of 50(w/w) % of the alcohol-in-oil type emulsion obtained in step v) and 50(w/w) % water, the conductivity is in the range of 4-18 ms/cm, such as in the range of 5-16 ms/cm, such as in the range of 6-15 ms/cm, such as in the range of 7-14 ms/cm, such as 8-13 ms/cm, such as 9-12 ms/cm, such as in the range of 10-11 ms/cm. When measuring the conductivity on a mixture of 50% (w/w) alcohol-in-oil type emulsion and 50% (w/w) water, the temperature of the mixture must be 20° C.

The Multivalent Metal Salt/the Buffering Component

The multivalent metal salt comprised in the invention may be any multivalent metal salt providing a high level of electrolytes in the alcohol-in-oil type emulsion. The multivalent metal salt may either be a salt of an organic and/or inorganic acid.

In an embodiment, the metal salt comprises a combination of a multivalent metal salt of an organic acid and a multivalent metal salt of an inorganic acid.

In a preferred embodiment, the multivalent metal salt is a combination of a multivalent metal salt having antiperspirant effect and a multivalent metal salt having a buffer effect. Typically, the multivalent metal salt having antiperspirant effect is an inorganic salt, where the multivalent metal salt having buffer effect is a multivalent metal salt of an organic acid.

From the prior art, it is well known that $AlCl_3$ is an effective antiperspirant salt and most of the commercially available antiperspirant compositions contain $AlCl_3$ as the active component, e.g. dissolved in a suitable solvent. $AlCl_3$ exerts its antiperspirant activity by reacting with water from the sweat to form aluminium hydroxychloride which acts as an astringent and thereby reduces the sweat output of the sweat glands. However, the disadvantage of using $AlCl_3$ is that the reaction with water from the sweat to form aluminium hydroxychloride also generates hydrochloric acid as a side product which may cause local skin irritation because of the high acidity. Additionally, clothes in contact with the application area may also be damaged, and both of these adverse effects can be ascribed to the formation of hydrochloric acid on the skin and in the sweat ducts.

The problems that appear from the high acidity of hydrochloric acid may be overcome e.g. by allowing the hydrochloric acid to react with a salt of the weaker acid, such as an organic acid, with no pK value below 2.5, the weaker acid then, according to well known principles, being liberated from the salt by the stronger hydrochloric acid to give the free weaker acid and a chloride instead. Such a salt of a weaker acid is referred to as a buffer salt. The fact that an aluminium salt of the weaker acid may be used, has the advantage of resulting in the formation of a further amount of aluminium hydroxychloride, thereby resulting in a further antiperspirant effect. On the other hand, the acidity is lowered considerably since the free acid present in the skin environment is now not solely hydrochloric acid but is in effect the weaker acid with no pK value below 2.5, the aluminium salt of which forms part of the composition of the invention. Since a weaker acid is less irritant to the skin, the net result is a reduction in or elimination of the skin irritation.

In order to prevent premature reaction of the aluminium chloride with water from the sweat, it is preferred that the composition is anhydrous. This is in particular obtained by using a carrier system, which is anhydrous or has no available water so that aluminium chloride does not undergo hydrolysis to aluminium hydroxychloride and hydrochloric acid.

The terms "no available water" and "substantially free from water" are used interchangeably and are intended to mean that the water present in the formulation is not able to solvate the aluminium salts, either because the water is present in too small an amount, or because the water is bound too strongly by another component in the composition. Thus, $AlCl_3$ will for example not undergo hydrolysis in 95% ethanol or in liquid sorbitol.

A preferred composition may be one in which the weaker acid/acids has/have no pK value below 4, in particular not below 3.5, especially not below 3. The use of an acid or acids with such properties will ensure a significant reduction in the level of skin irritation. The acid or acids is/are preferably physiologically acceptable.

Since a number of organic acids have various biological properties, it is preferred that an acid in the composition of the invention has a biological effect such as astringent, antibacterial, antimicrobial, antiseptic, antifungal, antiparasitic, antiperspirant, deodorant, antiinflammatoric, emollient, anesthetic, hemostatic, antipruritic properties, etc. By using an aluminium salt of one or more acids with one or more such properties, the properties of the composition of the invention may be amplified as well as expanded in its spectrum. Thus, if the acid used in the composition of the invention has antifungal properties, the composition of the invention could be useful in therapy or profylactic treatment of Tinea pedis, also known as "athlete's foot". This affliction is extremely common and is associated with sweating, and the maceration of the skin by the sweat facilitates the infection and makes it more difficult to treat. Even in persons with "normal" sweating it is desirable to reduce the amount of perspiration when treating the fungi.

Potentially useful acids with no pK value in aqueous solutions below 2.5 are the following: acetic, propionic, citric, acetylsalicylic, benzoic, salicylic, ascorbic, nicotinic, tartaric, phtalic, lactic, fatty acids (oleic, linoleic, undecenoic, octanoic, palmitic, ricinoleic, stearic, etc.), acetylcretosinic, succinic, carbamoylphenoxyacetic, diacetylsalicylic, anthranilic, mefenamic, gentisic, tolfenamic, acetotartaric, agaric, formic, subacetic, ellagic, fumaric, malic, morrhuic, oxalic, para-amino-benzoic, gallic, cinnamic, isoascorbic, sorbic, aminocaproic, aminomethylbenzoic, tranxenamic acid, naturally occurring amino acids such as glycine, alanine, valine, leucine, isoleucine, serine or threonine, etc, and derivatives thereof as well as tar acids, phenol, thymol and cation exchange resins. The term "derivatives thereof" is intended to mean that the various acids listed may also be further substituted with various groups, the presence of derivative substituents conferring one or more of the biological properties mentioned above to the acid in question. The substituent groups forming the derivatives may be selected from a broad range such as phenyl, phenylamino, naphtyl, benzoyl, indenyl or various heterocyclic groups such as indolyl, benzoxazolyl, pyridyl, benzindolyl etc., the substituent groups optionally themselves being substituted with substituents such as halogen, alkyl, alkoxy, optionally alkylsubstituted amino etc.

Thus, various derivatives of propionic, acetic, phenylacetic, salicylic, and anthranilic acid etc. are able to inhibit prostaglandin synthesis and can therefore function as local antiinflammatoric agents. Examples of propionic acid derivatives are naproxen, ibuprofen, benoxaprofen, and bucloxic acid; examples of phenylacetic and acetic acid derivatives are indomethacin, bufexamac, diclofenac, sulindac, and aclofenac; examples of salicylic acid derivatives are aspirin, acetaminosalol, diflunisal, dipyrocetyl, and fendosal; examples of anthranilic acid are etofenamic acid, flufenamic acid, meclofenamic acid, and tolfenamic acid; and an example of butyric acid derivatives is fenbufen.

Among the acids listed above, several are known to have some of the biological properties mentioned above. Thus, salicylic, acetotartaric, agaric, formic, subacetic and ellagic acid are known to have astringent properties, and undecenoic, octanoic, propionic, tolfenamic, isoascorbic and sorbic acid are known to have antifungal properties.

Preferred examples of acids having no pK value below 2.5 are acetylsalicylic, salicylic, benzoic, propionic, octanoic, undecanoic, sorbic acid, ascorbic acid, lactic acid, malic acid, stearic acid, citric acid, phthalic acid, tartaric acid, or a naturally occurring amino acid.

In order to ensure satisfactory neutralization of any hydrochloric acid liberated as a result of the reaction between $AlCl_3$ and water from the sweat, the molar ratio between the aluminium salt or salts of the acid or acids and $AlCl_3$ is preferably in the range from 1:1 to 1:2, in particular about 2:3.

In order to provide a composition effective for antiperspirant purposes, it is preferred that the AlCl$_3$ and the aluminium salt of the acid may be present in the composition of the invention in amounts corresponding to a total aluminium content of up to 3 gram atoms of Al per kilogram of composition, in particular from 1.0 to 2.0 gram atoms Al per kg composition.

The carrier or carriers in which the AlCl$_3$ and the aluminium salt of the weaker acid is dissolved and/or dispersed may be any of the carriers traditionally used for incorporation into antiperspirant compositions. Thus, the carrier may be a liquid, a gel, a semisolid or a powder. Liquid carriers may be alcohols, glycols, fats, fatty acid esters, fatty acids, paraffins, liquid polymers (such as silicone oil), for example ethyl alcohol, isopropyl myristate, glycerine, propylene glycol, etc. as well as mixtures thereof. A gel carrier may be an alcohol or another of the above mentioned liquid carriers such as ethyl alcohol containing a cellulose derivative such as hydroxypropyl cellulose. A semisolid carrier may be a polyglycol, a paraffin (for example vaseline), fats, or any of the above mentioned liquids containing a polymer such as liquid paraffin containing dissolved polyethylene (marketed under the trade name Plastibase). A solid carrier may be talc, starch, kaolin etc.

The composition of the invention may be prepared by methods commonly used within the art for the preparation of antiperspirant compositions, the preparation ordinarily comprising simply mixing together the constituents. Thus, a liquid composition may be prepared by dissolving or dispersing the aluminium chloride and the weaker acid/acids in the liquid carrier; optionally, the aluminium chloride and the weaker acid/acids may be dissolved or dispersed separately in two portions of the carrier or in two different carrier components followed by mixing of the mixtures. A gel composition may be obtained by starting from a liquid composition and adding gelling agent such as the above mentioned cellulose derivative.

In a preferred embodiment, an active antiperspirant multivalent metal salt and/or the buffering component is comprised in an alcohol-in-oil type emulsion. In such an alcohol-in-oil type emulsion the combined multivalent metal salt comprised are in an amount in the range of 5 to 50% w/w of the alcohol-in-oil type emulsion, such as a range of 8 to 40% w/w, e.g. in the range of 10 to 40% w/w, such as an range of 15 to 35% w/w.

The multivalent metal salt may comprise a metal ion.

Therefore, in some embodiments the metal ion to be comprised in the alcohol-in-oil type emulsion may be selected from the group consisting of Aluminium (Al), Iron (Fe), Zirconium (Zr), Calcium (Ca), Cupper (Cu), Magnesium (Mg), Titanium (Ti), Lead (Pb), Tin (Sb) and hydrates thereof.

In a preferred embodiment, the alcohol-in-oil type emulsion comprises an aluminium salt. Such an aluminium salt is preferably an aluminium salt having antiperspirant effect.

Aluminium salts known in the art to have antiperspirant effect comprises an active aluminium compound selected from the group consisting of aluminium chloride, aluminium chlorohydrate, aluminium chlorohydrex PEG (aluminium chlorohydrex polyethylene glycol), aluminium chlorohydrex PG (aluminium chlorohydrex propylene glycol), aluminium chlorohydrate, aluminium dichlorohydrate, aluminium dichlorohydrex PEG (aluminium dichlorohydrex Polyethylene Glycol), aluminium dichlorohydrex PG (aluminium dichlorohydrex propylene glycol), aluminium sesquichlorohydrate, aluminium sesquichlorohydrex PEG (aluminium sesquichlorohydrex polyethylene glycol), aluminium sesquichlorohydrate PG (aluminium sesquichlorohydrate propylene glycol), aluminium sulphate (aluminium sulphate buffered), aluminium zirconium octachlorohydrate, aluminium zirconium octachlorohydrex GLY, aluminium zirconium pentachlorohydrate, aluminium zirconium pentachlorohydrex GLY, aluminium zirconium tetrachlorohydrate, aluminium zirconium tetrachlorohydrex GLY, aluminium zirconium trichlorohydrate, aluminium zirconium trichlorohydrex GLY and any combination thereof, or any other FDA approved antiperspirant agents or a combination of said agents which list of agents is frequently updated.

In one embodiment, the alcohol-in-oil type emulsion comprises an aluminium salt having a buffer effect. In a preferred embodiment, the aluminium buffer may by aluminium lactate.

In a preferred embodiment of the present invention the alcohol-in-oil type emulsion comprising an aluminium salt wherein the aluminium salt is a combination of an active aluminium salt and an aluminium buffer, such as a combination of aluminium chloride and aluminium lactate.

In an embodiment of the present invention, the multivalent metal salt may be present as a hydrate, such as an aluminium salt hydrate, in particular in the form of aluminium chloride hexahydrate.

In an embodiment, the aluminium salt may be present in an amount in the range of 5 to 50% w/w, such as a range of 10 to 40% w/w, such as an range of 15 to 35% w/w, wherein the content of the aluminium salt is relative to the total amount of the alcohol-in-oil type emulsion.

In another embodiment of the present invention the alcohol-in-oil type emulsion comprises a multivalent metal salt, wherein the multivalent metal salt comprises ferric chloride or zirconium powder or any combination thereof.

In still other embodiments, the alcohol-in-oil type emulsion comprises a metal ion selected from the group consisting of Aluminium (Al), Iron (Fe), Zirconium (Zr), Calcium (Ca), Cupper (Cu), Magnesium (Mg), Titanium (Ti), Lead (Pb), Tin (Sb) or hydrates thereof. In such embodiments, the multivalent metal salt may have other effects than antiperspirant effects. In some of those embodiments the alcohol-in-oil type emulsion may be intended as a paint, such as an antifungal paint or for still other purposes.

In a preferred embodiment, the alcohol-in-oil type emulsion comprises a multivalent metal salt of an inorganic acid, in particular when that multivalent metal salt may be aluminium chloride or a hydrate thereof.

The Lower Alcohol

The alcohol-in-oil type emulsion typically comprises a lower-alcohol present in a discontinuous phase, where the oil phase typically is present in a continuous phase. In a preferred embodiment the alcohol present in the discontinuous alcohol phase is a lower alcohol such as an alcohol having 1-10 carbonatoms, such as an alcohol having 2-8 carbonatoms, e.g. an alcohol having 2-6 carbonatoms, such as an alcohol having 2-4 carbonatoms.

In the context of the present invention, the term "discontinuous phase" relates to the alcohol phase because the alcohol phase is being suspended in the oil phase in parts. Thus, these parts of the alcohol phase are not connected.

In the context of the present invention, the term "continuous phase" relates to the oil phase because this phase is substantially one coherent phase surrounding the alcohol phase.

In an embodiment, the alcohol phase comprises a lower-alcohol phase, said lower alcohol comprised herein may be a mono- or di-alcohol.

In an embodiment, the alcohol phase comprises a lower-alcohol phase, said lower alcohol comprised herein may be an alcohol having an unbranched carbon chain.

In an embodiment, the alcohol phase comprises a lower-alcohol phase, said lower alcohol comprised herein may be selected from the group consisting of ethanol, 1-propanol, 2-propanol, ethyleneglycol, 1-butanol, 2-butanol or any combination thereof.

In an embodiment, the alcohol phase comprises a content of an alcohol, such as a lower alcohol in an amount so that the content of the lower-alcohol phase relative to the total amount of the alcohol-in-oil type emulsion is in the range of 45-95% (w/w), 55-85% (w/w), such as 65-75% (w/w).

The Oil Phase

Preferably, the alcohol-in-oil type emulsion comprises a continuous oil phase, wherein the oil phase comprises one or more oil and/or fat products selected from a hydrogenated oil obtained from a vegetable source or any derivative thereof or any similar products synthetically produced. In an embodiment of the present invention the oil phase comprises the combination of two or more products selected from a hydrogenated oil from a vegetable source and any derivative thereof or any similar synthetically produced products, e.g. three or more products selected from a hydrogenated oil from a vegetable source and any derivative thereof or any similar synthetically produced products.

Furthermore, one or more additive(s) may be added to the oil phase. Said additive(s) may be selected from the group of components consisting of a siloxane, a silane, a wax, an ester of a fatty acid, a glycerol ester and any derivative thereof or any similar synthetically produced components of this group. In an embodiment of the present invention the oil phase comprises the combination of the hydrogenated oil obtained from a vegetable source and any derivative thereof or any similar synthetically produced products and two or more components, e.g. three or more components, such as four or more components, e.g. five or more components, such as six or more components, e.g. seven or more components.

In a preferred embodiment of the present invention the hydrogenated oil obtained from a vegetable source may be a Hydrogenated Castor Oil or any derivative thereof or any similar synthetically produced products.

In an embodiment, the alcohol-in-oil type emulsion comprises an oil phase in an amount so that the content of the oil phase relative to the total amount of the alcohol-in-oil type emulsion is in the range of 0-20% (w/w), such as in the range of 0.05-20% (w/w), e.g. in the range of 0.1-20% (w/w), such as in the range of 0.5-20% (w/w), e.g. in the range of 1-20% (w/w), such as in the range of 3-15% (w/w), e.g. in the range of 5-10% (w/w), such as 1-5% (w/w), e.g. in the range of 1-20% (w/w), such as in the range of 1-15% (w/w), e.g. in the range of 2-10% (w/w), such as 3-5% (w/w).

The Product

The product of the invention is characteristic in that the alcohol-in-oil type emulsion of the product processes a high emulsion stability providing a high homogeneity of the multivalent metal salt in the alcohol-in-oil type emulsion. This high level of stability is demonstrated when storing the product and subsequently to the storage, measuring the phase separation of the type emulsion.

Thus, the alcohol-in-oil type emulsion according to the present invention has a phase separation of at the most 10 mm, such as at the most 5 mm, e.g. at the most 3 mm, such as at the most 1 mm, e.g. at the most 0.7 mm, such as at the most 0.5 mm, e.g. at the most 0.4 mm, such as at the most 0.3 mm, e.g. at the most 0.2 mm, such as at the most 0.1 mm, where the phase separation is resulting after storage for 1½ month and measured on an amount of 0.5 l alcohol-in-oil type emulsion contained in a vessel having an inner diameter of 6.8 mm.

Alternatively, when storing the alcohol-in-oil type emulsion for a longer storage period, the alcohol-in-oil type emulsion has a phase separation of at the most 5 mm, e.g. at the most 1 mm, where the phase separation is resulting after storage for ½ month, such as 1 month, e.g. 1½ month, such as 2 month, e.g. 3 month, such as 4 month, e.g. 5 month, such as 6 month, e.g. 12 month, and measured on an amount of 0.5 l alcohol-in-oil type emulsion contained in a vessel having an inner diameter of 6.8 mm.

A main reason for this minor phase separation that might occur may be caused by evaporation of the alcohol phase during day-time and subsequent condensation of the alcohol phase during the night-time. Thus, significant improvements of the phase separation may be obtained if the alcohol-in-oil type emulsion is stored under conditions with no, or limited influence of temperature and light.

When referring to a "homogeneous" alcohol-in-oil type emulsion or a "homogeneous" mixture or "homogeneous" in any other context of the present invention it is to be understood as the phases comprised in the composition are uniformly distributed and/or that the particles are uniformly distributed throughout the composition. As used herein the term "homogeneous" is further to be understood as that the suspended particles do not sediment and that the phases of the emulsion do not, or substantially not, separate substantially.

In an embodiment of the present invention the alcohol-in-oil type emulsion, the antiperspirant or the product obtained in steps iii) or v) of the present invention may be substantially free of water.

Further, it may be characteristic for the alcohol-in-oil type emulsion to have a density in the range of 1.02-0.82 g/ml, such as in the range of 0.87-0.97 g/ml, such as in the range of 0.90-0.95 g/ml.

As used herein, the term "density" is to be understood as the weight of the alcohol-in-oil type emulsion measured as g pr ml. The measurement is carried out at 20° C.

In a preferred embodiment of the present invention, the alcohol-in-oil type emulsion, the antiperspirant or the product obtained in steps iii) or v) has a pH-value in the range of 0-5, such as in the range of 0-4, such as in the range of 0-3, such as in the range of 1-5, such as in the range of 2-3, when measuring on a mixture of 50% (w/w) alcohol-in-oil type emulsion (or the antiperspirant or the product obtained in steps iii) or v)) and 50% (w/w) water at 20° C.

In a further embodiment of the present invention, the alcohol-in-oil type emulsion, the antiperspirant or the product obtained in steps iii) or v) has a conductivity in the range of 4-18 ms/cm, such as in the range of 5-16 ms/cm, such as in the range of 6-15 ms/cm, such as in the range of 7-14 ms/cm, such as 8-13 ms/cm, such as 9-12 ms/cm, such as in the range of 10-11 ms/cm, when measuring on a mixture of 50% (w/w) alcohol-in-oil type emulsion (or the antiperspirant or the product obtained in steps iii) or v)) and 50% (w/w) water at 20° C.

In an embodiment according to the present invention an alcohol-in-oil type emulsion is provided which comprises at least 3, such as at least 4, e.g. at least 5, such as at least 6, e.g. at least 7, such as at least 8 of the components selected from the group consisting of an alcohol, such as ethanol, a salt of an organic acid, such as aluminium lactate, a salt of an inorganic acid, such as aluminium chloride, a siloxane derivative, such as cyclopentasiloxane, a glyceryl ester, such as glyceryl stearate, a cetyl ester, such as cetyl pallmitate, a wax, such as microcrystalline wax and an oil such as hydrogenated caster oil.

A stable alcohol-in-oil type emulsion may be achieved, when the ratio between the alcohol phase and the oil phase are within well-defined limits. A too high level of alcohol may result in a reversion of the phases from the alcohol-in-oil type emulsion to an oil-in-alcohol type emulsion. This is because increased levels of alcohol in the alcohol-in-oil type emulsion may pull the emulsifier out of the interface between the alcohol phase and the oil phase and result in the formation of flocculates and the alcohol-in-oil type emulsion may collapse. Therefore the alcohol-in-oil type emulsion may comprise an alcohol in an amount within the range of 45-95% (w/w), such as in the range of 55-85% (w/w), such as in the range of 65-75% (w/w).

In an embodiment, the alcohol-in-oil type emulsion comprises a multivalent metal salt as a buffer salt; when said buffer salt is present as aluminium lactate, the aluminium lactate is present in an amount in the range of 4-17% (w/w), such as 5-16% (w/w), such as 6-15% (w/w), such as 7-14% (w/w), such as 8-13% (w/w), such as 7-12% (w/w).

In an embodiment, the alcohol-in-oil type emulsion comprises an active aluminium compound; when said active aluminium compound is an aluminium salt, the aluminium salt is present in an amount in the range of 4-17% (w/w), such as 5-16% (w/w), such as 6-15% (w/w), such as 7-14% (w/w), such as 8-13% (w/w), such as 7-12% (w/w).

The alcohol-in-oil type emulsion may comprise an emollient. In an embodiment, the emollient comprises a siloxane derivative, such as cyclopentasiloxane in an amount in the range of 1-9% (w/w), such as 2-8% (w/w), such as 3-7% (w/w), such as 4-6% (w/w).

The alcohol-in-oil type emulsion may comprise an emulsifier. In an embodiment, the emulsifier comprises a glyceryl ester, such as glyceryl stearate in an amount less than 5% (w/w), such as less than 4% (w/w), such as less than 3% (w/w), such as less than 2% (w/w), such as less than 1% (w/w).

The alcohol-in-oil type emulsion may comprise a further emollient. In an embodiment, the emollient comprises a cetyl ester, such as cetyl palmitate in an amount less than 5% (w/w), such as less than 4% (w/w), such as less than 3% (w/w), such as less than 2% (w/w), such as less than 1% (w/w).

The alcohol-in-oil type emulsion may comprise a viscosity controlling agent. In an embodiment, the viscosity controlling agent comprises a wax, such as microcrystalline wax in an amount less than 5% (w/w), such as less than 4% (w/w), such as less than 3% (w/w), such as less than 2% (w/w), such as less than 1% (w/w).

The alcohol-in-oil type emulsion may comprise an oil, such as hydrogenated caster oil, in an amount less than 5% (w/w), such as less than 4% (w/w), such as less than 3% (w/w), such as less than 2% (w/w), such as less than 1% (w/w). In an embodiment of the present invention this oil may act as a viscosity controlling agent.

The alcohol-in-oil type emulsion may be formulated as an antiperspirant. In a preferred embodiment, the antiperspirant comprising an aluminium salt, a lower alcohol phase and oil phase.

Further Embodiments

The alcohol-in-oil type emulsion of the present invention is unique therein that the emulsion is stable despite a high level of ions and/or electrolytes. Therefore the alcohol-in-oil type emulsion of the present invention is applicable whenever a stable emulsion comprising a high level of ions are desired. The alcohol-in-oil type emulsion comprising a high level of ions may therefore find use in paint or a cosmetic product, such as an antiperspirant, a shampoo or a body lotion.

As will be understood from the above, the alcohol-in-oil type emulsion may be used as an antiperspirant.

That is, that in an embodiment the alcohol-in-oil type emulsion may be used as an antiperspirant for the reduction of perspiration.

Such a reduction of perspiration may be obtained under the arms, in the hands or under or on the feet of a human.

Resulting from the use as an antiperspirant the alcohol-in-oil type emulsion may be used for the reduction of unwanted odour.

Especially, the use of the alcohol-in-oil type emulsion as an antiperspirant may treat or elevate symptoms of hyperhidrosis.

In an embodiment of the present invention the temperature of the alcohol-in-oil type emulsion provided and/or during production may not exceed 40° C. because the alcohol-in-oil type emulsion may shift to an oil-in-alcohol type emulsion.

EXAMPLES

Example 1

Manufacture of an Alcohol-in-Oil Type Emulsion Comprising an Active Aluminium Salt and an Aluminium Buffer Salt

|   |   | Amount w/w % |
|---|---|---|
| 1 | Cyclopentasiloxane | 5-10 |
| 2 | Microcrystalline Wax | <1 |
| 3 | Cetyl Palmitate | <1 |
| 4 | Glyceryl Stearate | <1 |
| 5 | Hydrogenated Castor Oil | <1 |
| 6 | Aluminum Lactate | 8-20 |
| 7 | Alcohol (Ethanol) | 30-40 |
| 8 | AlCl3 in alcohol (ethanol) 18% (w/v)/16.4% (w/w) | 40-50 |
|   | Total | 100.00 |

The weighed amount of excipient 1) is placed in a vessel. The excipient 2) is added under short agitation for 40 seconds at 23° C. Excipient 3) is added under short agitation for 40 seconds at 27° C. Excipient 4) is added under short agitation for 30 seconds at 28° C. Excipient 5) is added under agitation for 3 minutes and 40 seconds and the temperature is simultaneously increased to 39° C. and when the desired temperature is reached agitation is stopped. Resulting after leaving the mixture to rest a short while, the mixture of excipients 1) to 5) has a consistency between a cream and a lotion. Metal salt 6) and solvent 7) are mixed for 3 minutes at 20° C. to obtain a suspension of the metal salt in the solvent. The mixture of excipients 1) to 5) is gently added to the suspension of 6) and 7) under agitation for 3 minutes at 22° C. to provide a resulting mixture of excipients 1) to 7). The suspension of metal salt in alcohol 8) is gently added to the mixture of excipients 1) to 7) under agitation for 3 minutes at 23° C. Agitation will vary depending on the batch volume used and the alcohol-in-oil type emulsion comprising the active aluminium salt and the aluminium buffer salt is provided.

Example 2 pH and Conductivity Of an Alcohol-in-Oil Type Emulsion Comprising an Active Aluminium Salt and an Aluminium Buffer Salt Mixtures of the alcohol-in-oil type emulsion and water is provided and the pH and conductivity is measured on the resulting mixture.

The obtained results are listed in the table:

| Added water | 40% (w/w) | 50% (w/w) | 80% (w/w) |
|---|---|---|---|
| pH | 2.20 | 2.37 | 2.96 |
| Conductivity (ms/cm) | 8.74 | 10.52 | 11.63 |

Example 3

Stability of the Composition of the Present Invention

A stability test was performed for the alcohol-in-oil type emulsion provided in the same manner as in example 1.

The alcohol-in-oil type emulsion was provided in the same manner as in example 1 was incubated at 25° C. in a 25 ml bottle. After 1 week the bottles was removed from the incubator and the stability was evaluated. After inspection the bottles was put back into the incubator for additional 1 week (a total of 2 weeks). After 2 weeks the bottles was removed once more from the incubator and the stability was evaluated again. The test was repeated 4 times.

Results

| Test no. | 1 week of rest at 25° C. temp. | 2 weeks rest at 25° C. temp. |
|---|---|---|
| 1 | Homogenous liquid and no phase separation | Homogenous liquid and no phase separation |
| 2 | Homogenous liquid and no phase separation | Homogenous liquid and no phase separation |
| 3 | Homogenous liquid and no phase separation | Homogenous liquid and no phase separation |
| 4 | Homogenous liquid and no phase separation | Homogenous liquid and no phase separation |

Conclusion

The above result shows that the alcohol-in-oil type emulsion provided by the present invention is stable and homogenous even the presence of a high content of a multivalent salt (Aluminum Lactate and $AlCl_3$) where there are no phase separation after resting in 2 weeks.

Example 4

An accelerated stability test was performed at 30° C. for the alcohol-in-oil type emulsion provided in the same manner as in example 1 and the alcohol-in-oil type emulsion was analysed after 24, 48, 72 and 96 hours.

The alcohol-in-oil type emulsion was provided in the same manner as in example 1 was incubated at 30° C. in a 25 ml bottle. After 24, 48, 72 and 96 hours a bottle was removed from the incubator, cooled to room temperature and the analysed.

At the time of incubation (0 hours) the content of Al-Lactate and $AlCl_3$ as well as the density was determined.

| Time | Al-Lactate | $AlCl_3$ | Density |
|---|---|---|---|
| 0 hours | 10.34% (w/w) | 10.27% (w/w) | 0.9191 |

Results

| Analysis | 24 timer | 48 timer | 72 timer | 96 timer |
|---|---|---|---|---|
| Weight before incubation | 44.20 g | 46.09 g | 44.92 g | 44.56 g |
| Weight right after incubation | 44.20 g | 46.07 g | 44.91 g | 44.55 g |
| Weight after reached room temp. | 44.22 g | 46.07 g | 44.91 g | 44.55 g |
| Product appearance | Homogenous liquid | Homogenous liquid | Homogenous liquid | Homogenous liquid |
| Phase separation | No phase separation | No phase separation | No phase separation | No phase separation |
| Precipitation | No precipitation | No precipitation | No precipitation | No precipitation |
| Colour | White | White | White | White |
| w/w % $AlCl_3$ (active ingredient) | 10.35% | 10.23% | 10.25% | 10.30% |
| w/w % Al-Lactate | 10.55% | 10.59% | 10.73% | 10.67% |
| Density | 0.9204 g/ml | 0.9172 g/ml | 0.9176 g/ml | 0.9183 g/ml |

Conclusion

The consistency in the weight before incubation, right after incubation (before cooling) and after the bottle reach room temperature demonstrates that there are no loss of product and the small differences in weight may be due to small variations during the test method.

The accelerated test also indicates a constantly homogenous liquid phase with no phase separation and with no precipitation and a constant density demonstrating stable alcohol-in-oil type emulsion having a high content of a multivalent salt (Al-Lactate and $AlCl_3$)

It is also demonstrated that the Al-Lactate and $AlCl_3$ are not subjected to any degradation or chemical reaction when contained in the alcohol-in-oil type emulsion as the amount of Al-Lactate and $AlCl_3$ remains constant.

Example 5

The stability of the alcohol-in-oil type emulsion of the present invention (in the following named product 2) may be compared to the antiperspirant composition described in the examples of EP 0 386 018 (in the following named product 1).

The products 1 and 2 are left in 500 ml bottles at room temperature and exposed to light during the daytime and in the dark and with a small temperature decrease of approximately 5° C. during the night time and without any shaking or movement.

| Incubation time | Product 1 | Product 2 |
| --- | --- | --- |
| Time = 0 | Vigorously shaking - Color: yellowish and milky appearance. 11 cm product 1 from the bottom to the top face of the product 1 and followed by 5 cm free space above the product 1 to the bottle cap. On the inside surface of the bottle, above the product 1 there are small flocculates distributed between several larger flocculates. | Vigorously shaking - Color: whitish and milky appearance. 11 cm product 2 from the bottom to the top face of the product 2 and followed by 5 cm free space above the product 2 to the bottle cap. On the inside surface of the bottle, above the product 2 there are formed a "buttermilk-like" layer of the product 2. |
| 10 minutes | Clear structural change of the product 1. Collection of larger flocculates which is floating in a slightly unclear liquid. | Color: whitish and milky appearance. On the inside surface of the bottle, above the product 2 there the "buttermilk-like" layer of the product 2 remains. There are observed no phase separation. |
| 2 hours 10 minutes | The flocculates are getting more and more dense but still "fluffy" and starts to move towards the bottom. The flocculates occupy app. 2/3 of the liquid. | Same as above after 10 minutes. |
| 3 hours and 10 minutes | The flocculates are still getting more and more dense but remains "fluffy" and starts gathering at the bottom. The flocculates occupy app. 1/2 of the liquid. | Same as above after 2 hours and 10 minutes. |
| 1 day 2 hours and 10 minutes | Approixmately 2 cm of the 11 cm is occipied by a precipitate formed from the flocculates that have moved to the bottom. The liquid on top of the precipitate remains slightly unclear with some small flocculates. | Same as above after 3 hours and 10 minutes. |
| 2 days 2 hours and 10 minutes | Precipitate as above, but the liquid above the precipitate is clearer and there are some flocculates. | Same as above after 1 day 2 hours and 10 minutes. |
| 3 days 2 hours and 10 minutes | Precipitate as above, but the liquid above the precipitate is even clearer (it is possible to look through) and there are some flocculates. | Same as above after 2 day 2 hours and 10 minutes. |
| 6 days 2 hours and 10 minutes | Precipitate as above, but the liquid above the precipitate is almost clear (it is possible to clearly look through) and there are few flocculates just above the precipitate. | Same as above after 3 day 2 hours and 10 minutes. But approximately 1 mm clear liquid is formed. |
| 7 days 2 hours and 10 minutes | The same as above after 6 days 2 hours and 10 minutes. | Same as above after 6 day 2 hours and 10 minutes. |
| 8 days 2 hours and 10 minutes | The same as above after 7 days 2 hours and 10 minutes. | Same as above after 7 day 2 hours and 10 minutes. |
| 9 days 2 hours and 10 minutes | The same as above after 8 days 2 hours and 10 minutes. But only very few small flocculates remains just above the precipitate. The precipitate may be shaken to a uniform appearance, however, after 10 minutes of rest flocculates starts to form again surrounded by a slightly unclear liquid. | Same as above after 8 day 2 hours and 10 minutes. However, the clear liquid formed has increased to approximately 2 mm The product 2 (e.g. after 8 day 2 hours and 10 minutes) may easily be mixed by gentle shaking or just by turning the bottle once or twiceto a homogenous and stable product. |

Conclusion

Product 1 forms an unstable formulation which after just 10 minutes starts to form flocculates/precipitate and separates into different phases.

Product 2 forms a stable formulation during the entire 9 days the experiment was performed. Only a very small phase separation of 2 mm clear liquid was observed (beginning after 6 days with 1 mm and reaching 2 mm after 9 days). This small phase separation is caused by condensation of the "carrier substance" the alcohol due to the small temperature variations during day and night time and has no influence on the stability of the product 2. The small phase separation may easily be neutralized by gentle shaking or just by turning the bottle once or twice and the homogenous and stable product reformed.

The invention claimed is:

1. An alcohol-in-oil type emulsion comprising
   i) a multivalent metal salt, wherein the content of the multivalent metal salt relative to the total amount of the alcohol-in-oil type emulsion is in the range of 5 to 40% (w/w)
   ii) a lower-alcohol phase
   iii) an oil phase,
   wherein said oil phase comprises one or more oil and/or fat products selected from a hydrogenated oil obtained from a vegetable source or any derivative thereof or any similar products synthetically produced, and wherein the content of the lower-alcohol phase relative to the total amount of the alcohol-in-oil type emulsion is in the range of 55-85%(w/w).

2. The alcohol-in-oil type emulsion according to claim 1, wherein the multivalent metal salt comprises an amount in the range of 10 to 40% w/w.

3. The alcohol-in-oil type emulsion according to claim 1, wherein the multivalent metal salt comprises a di- or tri- or tetra-valence metal-ion.

4. The alcohol-in-oil type emulsion according to claim 3, wherein the metal ion is selected from the group consisting of Aluminium (Al), Iron (Fe), Zirconium (Zr), Calcium (Ca), Cupper (Cu), Magnesium (Mg), Titanium (Ti), Lead (Pb), Tin (Sb) and hydrates thereof.

5. The alcohol-in-oil type emulsion according to claim 1, wherein the multivalent metal salt is an aluminium salt.

6. The alcohol-in-oil type emulsion according to claim 5, wherein the aluminium salt comprises an active aluminium compound selected from the group consisting of aluminium chloride, aluminium chlorohydrate, aluminium chlorohydrex PEG (aluminium chlorohydrex polyethylene glycol), aluminium chlorohydrex PG (aluminium chlorohydrex propylene glycol), aluminium chlorohydrate, aluminium dichlorohydrate, aluminium dichlorohydrex PEG (aluminium dichlorohydrex Polyethylene Glycol), aluminium dichlorohydrex PG (aluminium dichlorohydrex propylene glycol), aluminium sesquichlorohydrate, aluminium sesquichlorohydrex PEG (aluminium sesquichlorohydrex polyethylene glycol), aluminium sesquichlorohydrate PG (aluminium sesquichlorohydrate propylene glycol), aluminium sulphate (aluminium sulphate buffered), aluminium zirconium octachlorohydrate, aluminium zirconium octachlorohydrex GLY, aluminium zirconium pentachlorohydrate, aluminium zirconium pentachlorohydrex GLY, aluminium zirconium tetrachlorohydrate, aluminium zirconium tetrachlorohydrex GLY, aluminium zirconium trichlorohydrate, aluminium zirconium trichlorohydrex GLY and any combination thereof.

7. The alcohol-in-oil type emulsion according to claim 5, wherein the aluminium salt comprises an aluminium buffer, such as aluminium lactate.

8. The alcohol-in-oil type emulsion according to claim 5, wherein the aluminium salt comprises a combination of aluminium chloride and aluminium lactate.

9. The alcohol-in-oil type emulsion according to claim 5, wherein the aluminium salt is an aluminium salt hydrate.

10. The alcohol-in-oil type emulsion according to claim 5, wherein the content of the aluminium salt relative to the total amount of the alcohol-in-oil type emulsion is in the range of 7 to 12% w/w.

11. The alcohol-in-oil type emulsion according to claim 1, wherein the multivalent metal salt comprises ferric chloride or zirconium powder or any combination thereof.

12. The alcohol-in-oil type emulsion according to claim 1, wherein the lower-alcohol phase is an alcohol having 1-10 carbon atoms.

13. The alcohol-in-oil type emulsion according to claim 1, wherein the lower-alcohol phase is a mono- or di-alcohol.

14. The alcohol-in-oil type emulsion according to claim 1, wherein the lower-alcohol phase is an alcohol having an unbranched carbon chain.

15. The alcohol-in-oil type emulsion according to claim 1, wherein the lower-alcohol phase comprises an alcohol selected from the group consisting of ethanol, 1-propanol, 2-propanol, ethyleneglycol, 1-butanol, 2-butanol or any combination thereof.

16. The alcohol-in-oil type emulsion according to claim 1, wherein the content of the lower-alcohol phase relative to the total amount of the alcohol-in-oil type emulsion is in the range of 65-75% (w/w).

17. The alcohol-in-oil type emulsion according to claim 1, wherein the oil phase further comprises an additive selected from the group consisting of a siloxane, a silane, a wax, an ester of a fatty acid, a glycerol ester and any derivative thereof or any similar synthetically produced components of this group.

18. The alcohol-in-oil type emulsion according to claim 1, wherein the content of the oil phase relative to the total amount of the alcohol-in-oil type emulsion is in the range of 0.05-20%(w/w).

19. The alcohol-in-oil type emulsion according to claim 1, wherein the alcohol-in-oil type emulsion has a phase separation of at the most 10 mm, where the phase separation is resulting after storage for 1½ month and measured on an amount of 0.5 l alcohol-in-oil type emulsion contained in a vessel having an inner diameter of 6.8 mm.

20. The alcohol-in-oil type emulsion according to claim 1, wherein the alcohol-in-oil type emulsion has a phase separation of at the most 5 mm, where the phase separation is resulting after storage for ½ month, and measured on an amount of 0.5 l alcohol-in-oil type emulsion contained in a vessel having an inner diameter of 6.8 mm.

21. The alcohol-in-oil type emulsion according to claim 1, where the alcohol-in-oil type emulsion has a density in the range of 0.82-1.02 g/ml.

22. The alcohol-in-oil type emulsion according to claim 1, wherein the alcohol-in-oil type emulsion has a pH in the range of 0-5, when measuring on a mixture of 50% (w/w) alcohol-in-oil type emulsion and 50% (w/w) water at 20° C.

23. The alcohol-in-oil type emulsion according to claim 1, wherein the alcohol-in-oil type emulsion has a conductivity in the range of 4-18 ms/cm, when measuring on a mixture of 50%(w/w) alcohol-in-oil type emulsion and 50%(w/w) water at 20° C.

24. The alcohol-in-oil type emulsion according to claim 1, wherein the alcohol-in-oil type emulsion comprises an alcohol in an amount within the range of 65-75% (w/w).

25. The alcohol-in-oil type emulsion according to claim 1, wherein the alcohol-in-oil type emulsion comprises a buffer salt, such as aluminium lactate in an amount in the range of 4-17%(w/w).

26. The alcohol-in-oil type emulsion according to claim 1, wherein the alcohol-in-oil type emulsion comprises an active aluminium compound, such as an aluminium salt in an amount in the range of 4-17%(w/w).

27. The alcohol-in-oil type emulsion according to claim 1, wherein the alcohol-in-oil type emulsion comprises a siloxane derivative, such as cyclopentasiloxane in an amount in the range of 1-9%(w/w).

28. The alcohol-in-oil type emulsion according to claim 1, wherein the alcohol-in-oil type emulsion comprises a glyceryl ester, such as glyceryl stearate in an amount less than 5%(w/w).

29. The alcohol-in-oil type emulsion according to claim 1, wherein the alcohol-in-oil type emulsion comprises a cetyl ester, such as cetyl palmitate in an amount less than 5%(w/w).

30. The alcohol-in-oil type emulsion according to claim 1, wherein the alcohol-in-oil type emulsion comprises a wax, such as microcrystalline wax in an amount less than 5%(w/w).

31. The alcohol-in-oil type emulsion according to claim 1, wherein the alcohol-in-oil type emulsion comprises an oil, such as hydrogenated caster oil in an amount less than 5%(w/w).

32. The alcohol-in-oil type emulsion according to claim 1, wherein the alcohol-in-oil type emulsion is use in paint or a cosmetic product, such as an antiperspirant, a shampoo or a body lotion.

33. A method for using the alcohol-in-oil type emulsion according to claim 1 in an antiperspirant comprising incorporating the alcohol-in-oil type emulsion into an antiperspirant.

34. A method for reducing perspiration comprising applying the alcohol-in-oil type emulsion according to claim 1 to a surface of skin thereby causing the flow of sweat to the skin's surface to stop or to be reduced.

35. The use according to claim 34, wherein the reduction of perspiration is obtained under the arms, in the hands or under or on the feet of a human.

\* \* \* \* \*